(12) United States Patent
Rugnone

(10) Patent No.: US 10,209,191 B2
(45) Date of Patent: Feb. 19, 2019

(54) METHOD FOR IN-LINE QUANTITATIVE ANALYSIS OF A STREAM IN A PRODUCTION PLANT FOR THE SYNTHESIS OF UREA

(71) Applicant: Casale SA, Lugano (CH)

(72) Inventor: Luca Rugnone, Como (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/316,960

(22) PCT Filed: Jun. 2, 2015

(86) PCT No.: PCT/EP2015/062304
§ 371 (c)(1),
(2) Date: Dec. 7, 2016

(87) PCT Pub. No.: WO2015/189075
PCT Pub. Date: Dec. 17, 2015

(65) Prior Publication Data
US 2017/0102333 A1    Apr. 13, 2017

(30) Foreign Application Priority Data
Jun. 11, 2014 (EP) .................................. 14172011

(51) Int. Cl.
| | | |
|---|---|---|
| *G01J 3/44* | (2006.01) | |
| *G01N 21/65* | (2006.01) | |
| *C07C 273/04* | (2006.01) | |
| *G01N 21/84* | (2006.01) | |
| *G01N 21/85* | (2006.01) | |

(52) U.S. Cl.
CPC .......... *G01N 21/65* (2013.01); *C07C 273/04* (2013.01); *G01N 2021/8411* (2013.01); *G01N 2021/8416* (2013.01); *G01N 2021/8578* (2013.01); *Y02P 20/142* (2015.11)

(58) Field of Classification Search
CPC ....... G01N 21/8507; G01N 21/65; G01J 3/44; C07C 273/04
See application file for complete search history.

(56) References Cited

U.S. PATENT DOCUMENTS

| | | | | |
|---|---|---|---|---|
| 4,801,744 A | * | 1/1989 | Herman | ............ C07C 273/1809 528/422 |
| 9,273,016 B2 | * | 3/2016 | Kim | ..................... C07D 263/22 |

(Continued)

OTHER PUBLICATIONS

International Search Report issued in connection with PCT/EP2015/062304.

(Continued)

*Primary Examiner* — Maurice Smith
(74) *Attorney, Agent, or Firm* — Akerman LLP

(57) ABSTRACT

The invention discloses the use of Raman spectroscopy to analyze one or more process streams (5) of a urea synthesis production plant, where urea is synthesised from ammonia and carbon dioxide at high pressure (100-300 bar) and high temperature (50-250° C.). The radiation generated by the Raman scattering is analyzed to determine the concentration of components such as urea, ammonia and carbon dioxide in the process streams (5). A logic system implemented in a plant control unit (1) generates signals to target plant actuators to optimize the operation.

11 Claims, 2 Drawing Sheets

(56) References Cited

U.S. PATENT DOCUMENTS

| | | | | |
|---|---|---|---|---|
| 2004/0233425 | A1* | 11/2004 | Long | B01J 8/1809 |
| | | | | 356/301 |
| 2008/0092614 | A1* | 4/2008 | Ingels | B01J 19/242 |
| | | | | 71/30 |
| 2012/0220801 | A1 | 8/2012 | Salisbury et al. | |
| 2012/0282149 | A1* | 11/2012 | Mennen | B01J 10/00 |
| | | | | 422/187 |
| 2013/0033702 | A1* | 2/2013 | Tunheim | G01N 21/85 |
| | | | | 356/73 |

OTHER PUBLICATIONS

International Preliminary Report on Patentability issued in connection with PCT/EP2015/062304.

Van Eck, Martin, "Quantitative Analysis of the Urea Synthesis by Means of Laser Raman Spectrometry", Dissertation, May 28, 1985.

Buback, M. et al., "Raman Scattering of Pure Ammonia at High Pressures and Temperatures", The Journal of Physical Chemistry, vol. 80, No. 22, Oct. 1, 1976, pp. 2478-2482.

Adar, F. et al., "Raman Spectroscopy for Process/Quality Control", Applied Spectroscopy Reviews, vol. 32, No. 1/02, Feb. 1, 1997, pp. 45-101.

* cited by examiner

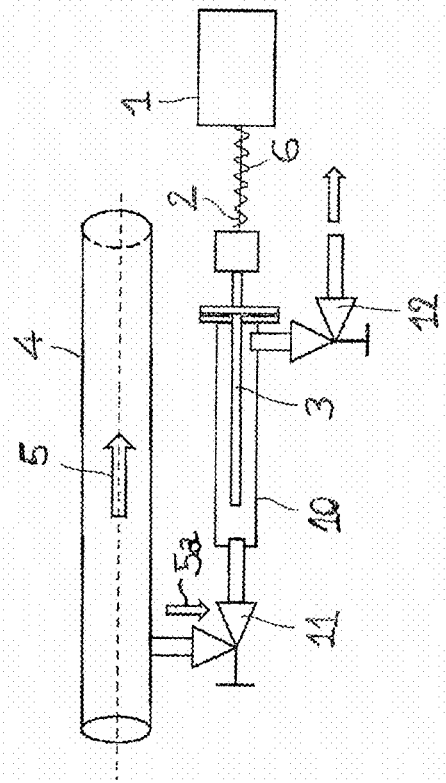
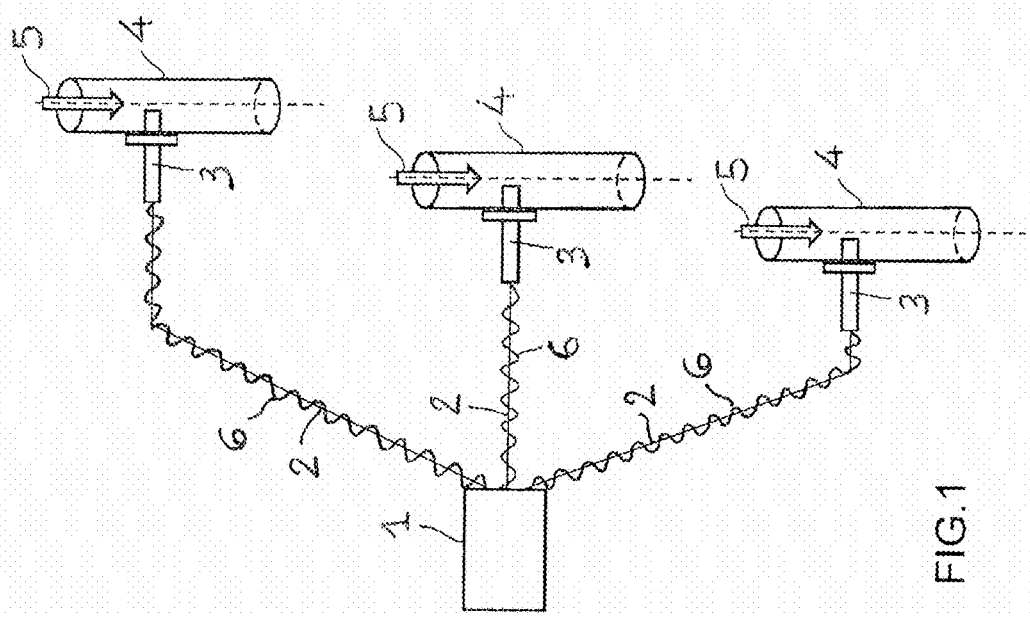
FIG.2
FIG.1

METHOD FOR IN-LINE QUANTITATIVE ANALYSIS OF A STREAM IN A PRODUCTION PLANT FOR THE SYNTHESIS OF UREA

This application is a national phase of PCT/EP2015/062304, filed Jun. 2, 2015, and claims priority to EP 14172011.0, filed Jun. 11, 2014, the entire contents of both of which are hereby incorporated by reference.

FIELD OF THE INVENTION

The present invention relates to the field of urea synthesis. More in detail, the invention relates to in-line quantitative analysis of process streams involved in the synthesis of urea in a production plant starting from ammonia and carbon dioxide at high pressure and high temperature.

PRIOR ART

Urea is synthesized from ammonia and carbon dioxide. An overview of the related processes can be found in the Ullmann's Encyclopedia of Industrial Chemistry, $5^{th}$ revision, vol. A27, par. 3.3.

Several process streams are involved in the urea synthesis process, which is highly sensitive to their composition, in particular to the concentration of reactants such as ammonia and carbon dioxide, and to the concentration of water which is detrimental to the yield at equilibrium. Parameters which strongly influence the process include, for example, the ammonia to carbon molar ratio, the water to carbon molar ratio and the carbon conversion to urea. Hence, the reactants concentration should be ideally controlled in a tight range, in order to obtain the optimum performance and the maximum yield.

Preferably the industrial urea synthesis is carried out according to the so-called total recycle technology. Most preferably nowadays the urea synthesis is operating according to the so-called stripping technology.

The main items of a stripping plant include a high-pressure synthesis reactor, a stripper, a carbamate condenser and possibly a scrubber, which form a high pressure loop, and one or more recovery sections operating at a lower pressure. The above referred process streams include for example the effluent of the reactor, of the carbamate condenser or of the scrubber, the concentrated solution leaving the stripper, the low pressure carbamate solution from the lower-pressure recovery sections.

For the above reasons, there is the need to monitor the composition of said process streams for a better understanding and optimization of the process, and in order to ensure a proper control of the plant.

The conventional technique consists in the off-line analysis of samples of one or more selected process stream(s). A sample of a pressurized process stream is extracted in a known amount of water to dissolve the gases which are developed by the depressurization from the reactive environment, then the sample is analyzed in a separate laboratory.

This technique has several drawbacks. Sampling of the stream must be performed by expert personnel due to safety reasons and is intrinsically affected by mistakes due to easy loss of volatile compounds. Off-line analysis introduces a time delay between the sampling and the analysis, being unsuitable to a prompt control of the process which is under continuous evolution. Another disadvantage is that the extraction of the sample causes a sudden change of thermodynamic parameters and affects the equilibrium and concentration of the evolving medium; as a consequence, the composition of the sample and the result of the analysis may be affected.

Due to the above reasons, there is an incentive to perform in-line analysis in order to get real-time data of the process stream concerned. In-line analysis however is challenging due to the corrosive nature of ammonium carbamate and transient products involved in the synthesis of urea, and due to the elevated temperature and pressure, particularly in the high-pressure loop. For example, the solution leaving the reactor is typically under supercritical conditions.

Prior attempts to perform in-line analysis include the use of a chromatographic technique for monitoring the gas phase from the reactor. This technique however is only applicable when the reactor has an independent outlet gas line. Moreover, the information about the composition of the gas phase has been found unsuitable for in-line control of the plant, because the formation of ammonium carbamate and formation of urea through the subsequent dehydration of carbamate evolve in the liquid phase. Another drawback is that the gas chromatographic technique requires expensive maintenance.

Taking all the above problems into account, the state of the art is to implement a process control mainly dependent on the ammonia to carbon molar ratio (N/C), which is indirectly measured as a function of density. Density can be measured in a relatively simple way, and the above N/C ratio has a linear dependence on density in a very narrow range of temperature and pressure. Hence, as long as the temperature and pressure are within a certain range, the N/C ratio can be estimated with acceptable accuracy and the technique is regarded as reliable.

The ratio between the moles of ammonia and carbon in the reactive mixture, however, is only one of the parameters which actually govern the process. For example this method is not able to provide information about the water to carbon ratio and converted carbon to urea. In addition, the N/C ratio is only measured via a model based on density readings. Said model is tuned for a narrow range of density and hence the accuracy may be affected when the actual density (depending on temperature and pressure) is outside said range or is close to the boundary values.

Another problem encountered in the control of a recycle urea process is the possible cascade effect caused by a change of a composition of a process stream. For example, the performance of the reactor is influenced by the composition of the carbamate recycle stream from the lower pressure recovery section while, on the other hand, the composition of said recycle stream is also depending on the composition of the urea solution at the outlet of the high pressure stripper which is feeding the recovery unit. A proper control system must be able to take into account this behavior.

Hence there is still the need of a method for in-line detecting of detailed information concerning the composition of mediums involved in the urea synthesis, to solve the above mentioned problems.

SUMMARY OF THE INVENTION

The purpose of the invention is to solve the above problems and in particular to provide a method and apparatus for a better quantitative analysis and better control and optimization of a urea plant.

The idea underlying the invention is the application of Raman spectroscopy to the in-line quantitative analysis of streams of a urea synthesis process.

Accordingly, a first aspect of the invention is a method of in-line quantitative analysis of at least one process stream of a urea synthesis process where urea is synthesized from ammonia and carbon dioxide, characterized by the use of Raman spectroscopy for said in-line quantitative analysis. Preferably said method is applied to a high-pressure and high-temperature synthesis process. More preferably, said method is applied to a urea process where synthesis pressure is 100 to 300 bar and temperature is 50 to 250° C. Hence said at least one process stream has preferably a pressure and temperature in the above ranges.

Raman spectroscopy is based on the effect known as Raman scattering. Raman scattering is a type of inelastic scattering of electromagnetic radiation such as a laser light when traversing a medium. The effect can be summarized as follows. The most of the incident photons undergo elastic scattering (termed Rayleigh scattering) resulting in the scattered radiation having the same frequency as the incident one. A minority of the incident photons, however, undergo inelastic scattering resulting in emitted photons having lower or higher energy, thus leading to frequencies above and/or below the incident beam.

The inelastic scattering is caused by a selective interaction between the radiation and the molecules, which is specific for each chemical bond. Hence, the frequency shift observed in the scattered radiation provides information about the composition of the medium, for example the concentration of a specific molecule. The weak inelastically scattered light is separated from the intense Rayleigh scattered light and is collected to get information about the composition of the medium. Accordingly, Raman spectroscopy can be defined as the spectrophotometric detection of the inelastically scattered light.

Preferably, the Raman spectroscopy of streams of urea process according to the invention is carried out with a laser beam. Said laser beam is preferably focused in the process stream to be analyzed. Preferably said laser beam is in the visible or near-visible range. Preferably said laser beam is monochromatic.

The visible range is understood as wavelengths of 390 to 700 nm. The near-visible range is understood as wavelengths between 300 nm and 1.4 microns. Hence, preferably the method of the invention is carried out with a monochromatic laser beam having a wavelength between 300 and 1400 nm and more preferably between 400 and 1000 nm. For example in a particularly preferred embodiment the process of the invention is carried out with a laser beam of 785 nm.

It has been found that the molecules involved in the synthesis of urea, including urea, ammonium carbamate, carbonate and hydrogen carbonates, and ammonia, provide selective and distinguishable Raman scattering. Hence, the Raman spectroscopy permits to gather quantitative information about the concentration in weight (wt %) of said compounds. The method of the invention can be used to determine the concentration of at least one of urea, carbon dioxide, and/or ammonia contained in the process stream.

A further aspect of the invention is a modelling of the chemistry of the solutions, which is of advantage for the application of Raman spectroscopy. Accordingly, the chemistry is modeled with reference to the following components:
a first component denotes the form of converted carbon in the carbonyl di-amidic formula;
a second pseudo-component denotes all forms of unconverted carbons such as carbamate, carbonate and hydrogen carbonate, etc. assumed as equivalent mono component;
a third pseudo-component denotes all forms of nitrogen not belonging to the urea molecule, free as ammonia or combined as ammonium hydroxide, or in the salts forms as ammonium carbonate, hydrogen carbonate and carbamate.

In the following description, the first component is also named urea; said second component is also named carbon dioxide, and said third component is also named ammonia. The above model can be applied to any process stream, for example to the solution effluent from the reactor or from the stripper.

The applicant has found that the urea concentration can be associated to a characteristic Raman band corresponding to the excitation of the carbonyl di-amide bond. The carbonyl di-amide bond is found in the molecule of urea and is targeted in the present invention to distinguish urea from other forms of not converted carbon such as carbon dioxide. Other forms of not converted carbon behaves differently to the Raman scattering being the atomic bonds within the molecule mostly in the carboxyl form (carbonate, hydrogen carbonate and carbamate).

Hence, a preferred feature of the invention is to detect the concentration of urea in a process stream by means of detection of a spectroscopy band corresponding to excitation of the carbonyl di-amide bond.

The concentration of carbon-containing molecules other than urea (non-converted carbon) can be determined as an equivalent concentration of carbon dioxide corresponding to the excitation of the atomic bonds in the carboxyl form.

According to one of the aspects of the invention, said components are detected as follows:
said first component ("urea") can be identified by excitation of the carbonyl di-amide bond with a Raman shift of a suitable incident laser light in the frequency range from 900 to 1050 $cm^{-1}$, said second component ("carbon dioxide") including the non-converted forms of carbon has been found to be Raman-reactive more particularly from 1000 to 1150 $cm^{-1}$,
said third component ("ammonia") including other forms of nitrogen (other than urea) can be detected by Raman excitation in a frequency range from 1350 to 1750 $cm^{-1}$.

The frequency ranges are indicated in $cm^{-1}$ as per common practice in the spectroscopy applications. Said incident laser light has preferably a wavelength of 785 nm.

In a complex mixture where urea and ammonium carbamate are blended together the mentioned range of frequency identifies all the nitrogen forms in the sample including the ones belonging to the urea molecule. Anyhow, said third pseudo-component of "ammonia" could be easily detected subtracting the "urea" contributes to the signal intensity once the "urea" concentration is known by its specific frequency.

The method can be applied to any industrial process for synthesis of urea at high pressure and high temperature including but not limited to total recycle processes and to stripping processes such as CO2-stripping and self-stripping. The method is preferably applied to processes where synthesis of urea takes place at a pressure in the range 100-300 bar and temperature in the range 50-250° C.

According to an embodiment, the Raman analysis is performed directly on a main stream. Accordingly, a suitable probe is installed directly on the pipe concerned. According to other embodiments, the analysis can also be performed on a side stream taken from a main pipe. This second option can be preferred to provide safer and easier inspection and maintenance of the system. In this second option, the probing system comprises preferably a sampling chamber.

Another aspect of the invention is a method for controlling a plant for the synthesis of urea according to the attached claims. The method for controlling a urea synthesis process makes use of Raman spectroscopy for real-time analysis of the composition of at least one, and better if more streams of said process. Said process can be any known urea process for industrial production including the non-stripping and stripping processes.

A further aspect of the invention is an apparatus for control and optimization of a urea synthesis plant according to the attached claims. Information provided by the Raman spectroscopy analysis are used for controlling and optimize automatically the plant.

The apparatus comprises one or more probes wherein the probe or each of the probes is arranged to focus a radiation from the emitter in a focus point, said focus point being in contact with one of said process streams, and to return the Raman-scattered radiation.

Preferably, the apparatus comprises high pressure optic probes focusing the laser in the outlet stream from the synthesis reactor, in the outlet urea solution stream from the high pressure stripper and in the carbamate recycle stream from the recovery section to the synthesis unit. A fiber optic connection between the probe and the instrument is preferably provided.

A considerable advantage of the invention is the in-line detection of the composition of streams involved in the urea synthesis and collection of real time information about the process performance not only in terms of molar ratio ammonia to carbon, but also in terms of water to carbon ratio and converted carbon to urea.

The invention provides a better optimization of the plant compared to prior art systems, by monitoring continuously the composition of convenient process streams which are bonded each other by cascade effect permitting the real time control of the plant to anticipate worsening effect which are expected to happen due to the composition and parameters changes of the fundamental streams The related benefits include: improvement of the overall stability of the process, minimization of the risk of shut down, increase of the yield of conversion, reduced energy consumption and reduced pollutants.

The features and advantages of the invention shall become clearer from the following description of preferred embodiments.

DESCRIPTION OF FIGURES

FIG. 1 is a scheme of a system for carrying out the method of the invention, according to a first embodiment.

FIG. 2 is a scheme of a system for carrying out the method of the invention, according to a second embodiment.

DETAILED DESCRIPTION OF A PREFERRED EMBODIMENT

Figure 3:
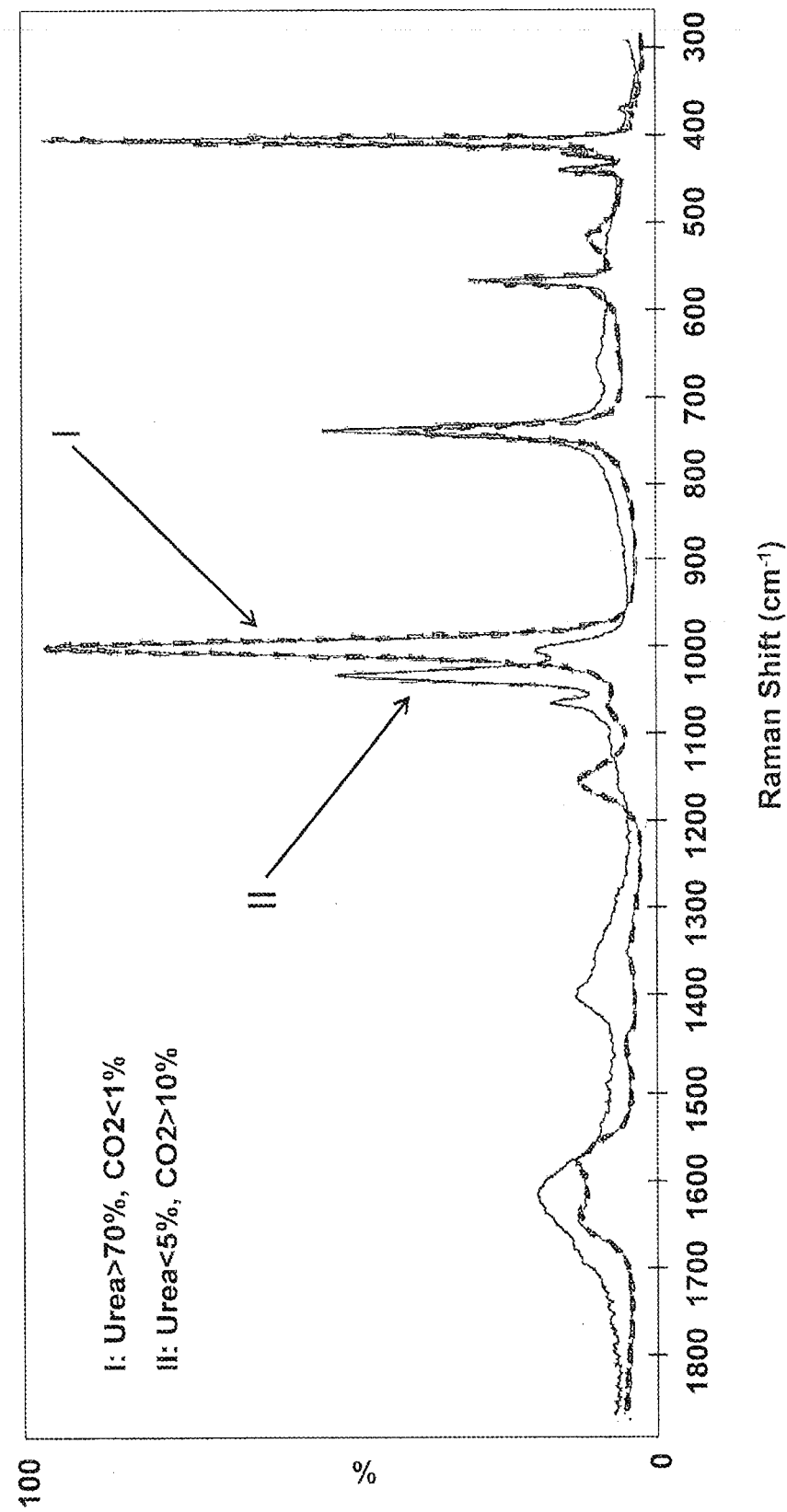
FIG. 3 is a plot of spectra of two process streams comprising different concentrations of urea and carbon dioxide.

FIG. 1 illustrates an apparatus according to an embodiment of the invention comprising a main control unit 1 and a plurality of probes 3 with relevant optical cables 2.

The probes 3 are mounted on selected process pipes 4 of a urea plant; each process pipe 4 carrying a respective process stream 5.

Said process pipes 4 can belong for example to the high-pressure synthesis loop or to the recovery section of a urea plant. The process streams 5 will comprise urea, water, ammonia, ammonium carbamate, carbon dioxide and possibly other chemical compounds involved in the synthesis.

For example the process pipes 4 may include one or more of: the effluent pipe of a reactor, carrying an aqueous solution of urea, unconverted carbamate and free ammonia; the effluent pipe from the high pressure stripper; the pipe of recycle carbamate at the delivery of the high pressure pump.

The process streams 5 may have an elevated temperature and pressure. Typically the process streams 5 have a pressure of up to 300 bar and a temperature of up to 250° C.

The main control unit 1 comprises a laser emitter and a suitable Raman analyzer connected to a control system of the urea plant. Said Raman analyzer is suitable to analyze scattered photons received from the probes 3.

More in detail, laser beams 6 emitted by the control unit 1 are conveyed to focus points of said probes 3 through the fiber optic cables 2. The focus points are determined in such a way that in each of them the incident light beam 6 is in contact with the fluid of the respective process stream 5.

Then, in accordance with the Raman effect, most of the incident light 6 undergoes elastic scattering (Rayleigh scattering), which means that the scattered photons will have the same wavelength of the incident ones; a minor part of the light 6 however undergoes Raman scattering and, as a consequence, will show a wavelength/frequency shift. The amount of said shift depends on the composition of the streams 5.

The scattered photons are conveyed back from the probes 3 to the main control unit 1 via said optical cables 2.

The intensity and wavelength of the detected Raman photons are used by said Raman analyzer, which is integrated in the main control unit 1, to measure the concentration of target compounds such as urea, carbon dioxide and ammonia.

FIG. 2 relates to another embodiment where the analysis is performed on a side stream 5a. In this embodiment, the system comprises a sampling chamber 10 connected to the process pipe 4 via an admission valve 11. The probe 3 is mounted on said sampling chamber 10. The side stream 5a is taken from the main pipe 4 and admitted to the chamber 10 via said valve 11. The Raman analysis is performed on the medium contained in the chamber 10, with the same method as described above. Then, the medium can be discharged via a discharge valve 12 to a lower pressure section of the plant or to any suitable location. This solution can be preferred because it is less invasive to the main pipe 4. Furthermore, the system can be safely accessed by closing the valve 11, without affection to the operation of the process pipe 4.

The FIG. 3 contains a first spectrum I which relates to a sample containing more than 70% urea and less than 1% of pseudo-component CO2 (as above defined), and a second spectrum II which relates to a sample containing less than 5% urea and more than 10% of pseudo-component CO2. The plot show the urea bands at around 1000 $cm^{-1}$ and the CO2 band (sample II) at around 1050 $cm^{-1}$. The bands at around 1400 and 1650 $cm^{-1}$ relative to the pseudo-component "ammonia" are also clearly visible.

The invention as described meets the above mentioned purpose. A logic system implemented in the plant control unit 1 generates signals to the target plant actuators to optimize the operation.

A disturbance in the composition of the urea solution at high pressure stripper outlet due to deviation of the operating parameters is going to impact with a dynamic the composition of the carbamate recycle stream and again after a certain dynamic the performance of the reactor and its outlet composition. If a deviation in the composition at the stripper outlet is detected the logic system can act to prevent the carbamate composition to change and finally affect the reactor performance.

EXAMPLE

An experimental study on process streams from an industrial plant for the production of urea has been carried out.

Said process streams have been selected opportunely to contain different concentration of urea, carbon dioxide and ammonia and have been subjected to the same analytical procedure as per following.

A ¼" optic probe and 785 nm laser light have been used. The laser light of 785 nm has been selected in this experimental campaign, nevertheless the application of the method could be also extended as a principle to other monochromatic laser lights as mentioned above. The optic has been connected to a Raman analyzer through 5 meters of fiber optic cable. The sample has been placed into a glass recipient of 10 ml volume. A light shielding system has been applied to isolate the sample from the environmental light contamination. Then, 1-minute photons have been acquired for each sample and the measure of each sample has been repeated for at least 5 times. The above procedure allowed to acquiring spectra as in FIG. 3 clearly showing the peaks corresponding to urea and to the pseudo-component of CO2.

The invention claimed is:

1. A method of in-line quantitative analysis of at least one process stream of a urea synthesis process where urea is synthesized from ammonia and carbon dioxide, at a pressure in the range of 100 to 300 bar and temperature in the range of 50 to 250° C., said method comprising the use of Raman spectroscopy for said in-line quantitative analysis, wherein:
the concentration of urea in said process stream is determined by Raman spectroscopy and through the detection of a spectroscopy band corresponding to excitation of the carbonyl di-amide bond;
the concentration in said process stream of carbon-containing molecules other than urea and having a carboxyl group is determined by Raman spectroscopy as an equivalent concentration of carbon dioxide corresponding to the excitation of the atomic bonds in the carboxyl form.

2. The method according to claim 1, wherein the Raman spectroscopy is carried out with a laser beam focused in said at least one process stream.

3. The method according to claim 2, wherein said laser beam has a wavelength in the visible or near-visible range between 300 and 1400 nm.

4. The method according to claim 1, wherein:
excitation of the carbonyl di-amide bond of molecules of urea is detected by means of Raman shift of an incident laser beam having a suitable wavelength, in a frequency range of 900 to 1050 cm−1, and
said molecules other than urea are detected by means of Raman shift of said incident laser beam, in a frequency range of 1000 to 1150 cm−1.

5. The method according to claim 4, wherein the concentration of ammonia is determined by means of Raman shift of said incident laser beam, in a frequency range of 1350 to 1750 cm−1.

6. The method according to claim 4, said incident laser beam having a wavelength of 785 nm.

7. The method according to claim 1, wherein the Raman spectroscopy is carried out directly on a process pipe carrying a process stream.

8. The method according to claim 1, wherein the Raman spectroscopy is carried out on a side stream taken from said process stream.

9. The method for controlling a plant for synthesis of urea, characterized by including a quantitative analysis of at least one process stream of said plant with the application of Raman spectroscopy according to claim 1.

10. The method for controlling a plant according to claim 9, wherein the Raman spectroscopy include the steps of:
sending an incident radiation, preferably a laser beam, to a focus point in at least one process stream;
receiving a scattered radiation;
analyzing the scattered radiation with a Raman spectroscope; and
using the detected composition of said process streams as input to a logic control system of the plant.

11. The method according to claim 2, wherein said laser beam has a wavelength in the visible or near-visible range between 400 and 1000 nm.

* * * * *